(12) United States Patent
Ishimaru

(10) Patent No.: US 8,988,689 B2
(45) Date of Patent: Mar. 24, 2015

(54) SPECTROSCOPIC MEASUREMENT DEVICE AND SPECTROSCOPIC MEASUREMENT METHOD

(75) Inventor: Ichiro Ishimaru, Takamatsu (JP)

(73) Assignee: National University Corporation Kagawa University, Takamatsu (JP)

( * ) Notice: Subject to any disclaimer, the term of this patent is extended or adjusted under 35 U.S.C. 154(b) by 36 days.

(21) Appl. No.: 13/820,592

(22) PCT Filed: Sep. 6, 2011

(86) PCT No.: PCT/JP2011/070273
§ 371 (c)(1),
(2), (4) Date: Apr. 18, 2013

(87) PCT Pub. No.: WO2012/033096
PCT Pub. Date: Mar. 15, 2012

(65) Prior Publication Data
US 2013/0215428 A1 Aug. 22, 2013

(30) Foreign Application Priority Data
Sep. 8, 2010 (JP) ................................. 2010-201221

(51) Int. Cl.
*G01J 3/45* (2006.01)
*A61B 5/00* (2006.01)
*G01J 3/02* (2006.01)
*G01J 3/453* (2006.01)
*A61B 5/145* (2006.01)
*A61B 5/1455* (2006.01)

(52) U.S. Cl.
CPC ............. *A61B 5/0075* (2013.01); *G01J 3/0208* (2013.01); *G01J 3/453* (2013.01); *G01J 3/021* (2013.01); *A61B 5/14532* (2013.01); *A61B 5/1455* (2013.01); *A61B 2562/0233* (2013.01)

USPC .......................................................... 356/451

(58) Field of Classification Search
CPC ............. A61B 2562/0233; A61B 3/00; A61B 5/0075; G01J 3/45; G01J 3/4531; G01B 9/0215; G01N 21/76
USPC ................................................. 356/452, 451
See application file for complete search history.

(56) References Cited

U.S. PATENT DOCUMENTS 5,495,334 A * 2/1996 Nagoshi et al. ............... 356/456
5,654,820 A * 8/1997 Lu et al. ........................ 359/298

(Continued)

FOREIGN PATENT DOCUMENTS

JP A-02-145927 6/1990
JP A-02-147842 6/1990

(Continued)

OTHER PUBLICATIONS

T. H. Barnes, "Photodiode array Fourier transform spectrometer with improved dynamic range", Nov. 15, 1985.*

(Continued)

*Primary Examiner* — Kara E Geisel
*Assistant Examiner* — Maurice Smith
(74) *Attorney, Agent, or Firm* — Oliff PLC

(57) ABSTRACT

Multiple rays such as scattered lights and fluorescent lights emitted radially in a variety of directions from each bright point in a measurement area enter an objective lens, where the multiple rays are converted into a parallel beam. The parallel beam is reflected by both a reference mirror unit and an oblique mirror unit, and the reflected beams pass through an imaging lens to form an interference image on a light-receiving surface of a detection unit. The detection of the light intensity of the interference image on the light-receiving surface enables an acquisition of the interferogram (the waveform of the change of imaging intensity) in which the light intensity continuously changes. By Fourier-converting the interferogram, spectral characteristics can be obtained which show the relative intensities for each wavelength of the lights emitted from one bright point of an object to be measured.

20 Claims, 5 Drawing Sheets

(56) References Cited

U.S. PATENT DOCUMENTS

| | | | |
|---|---|---|---|
| 6,636,317 B2 * | 10/2003 | Akikuni | 356/450 |
| 6,646,264 B1 | 11/2003 | Modiano et al. | |
| 6,985,232 B2 * | 1/2006 | Sezginer | 356/451 |
| 7,079,252 B1 * | 7/2006 | Debreczeny et al. | 356/451 |

FOREIGN PATENT DOCUMENTS

| | | | | |
|---|---|---|---|---|
| JP | B2-2676028 | | 11/1997 | |
| JP | A-2004-515778 | | 5/2004 | |
| JP | 2008309707 | * | 6/2007 | G01J 3/45 |
| JP | A-2008-309706 | | 12/2008 | |
| JP | A-2008-309707 | | 12/2008 | |

OTHER PUBLICATIONS

Marja-Leena Junttila, "Stationary Fourier-transform spectrometer", Jul. 20, 1992.*

Marja-Leena Juntilla "Stationary Fourier-transform spectrometer" Applied Optics Jul. 20, 1992.*

Fourier Henkan Sekigai Bunkoho (Fourier-transform Infrared Spectrometry), edited by Hiraishi Jiro, Gakkai Shuppan Center, pp. 1-3 and 12-33, Nov. 1985.

Ishimaru, Ichiro, "Trial for realization of the spectroscopic tomography of biomembrane," *Proceedings of the 22$^{nd}$ Bioengineering Conference*, 2009 Annual Meeting of BED/JSME, Cover and p. 359, Jan. 8, 2010.

Uraki et al., "Proposal of the One-shot real-time Fourier spectroscopic imaging," *Optics & Photonics Japan 2010 Extended Abstracts*, pp. 84-85, Nov. 8, 2010 (w/ English Abstract).

Li et al., Passive Laser Spectrum Detection Technology Based on Static Interferometer, *Proc. OfSPIE*, vol. 7160, Article 71601 I, 5 pages, Feb. 2, 2009.

Junttila, Marja-Leena, "Stationary Fourier-transform spectrometer," *Applied Optics*, vol. 31, No. 21, pp. 4106-4112, Jul. 20, 1992.

International Preliminary Report on Patentability Issued in Application No. PCT/JP2011/070273; Dated Nov. 13, 2012 (With Translation).

International Search Report issued in Application No. PCT/JP2011/070273; Dated Oct. 18, 2011 (With Translation).

* cited by examiner

LIGHT-RECEIVING SURFACE (IMAGING PLANE)
INTERFERENCE AREA
REFERENCE MULTIPLE RAYS
OBLIQUE MULTIPLE RAYS
APPROX. 1 DEGREE

SPECTROSCOPIC MEASUREMENT DEVICE AND SPECTROSCOPIC MEASUREMENT METHOD

TECHNICAL FIELD

The present invention relates to a spectroscopic measurement device and a spectroscopic measurement method which are useful in the field of life sciences, specifically for the component analysis of a moving measurement object, such as a biological membrane.

BACKGROUND ART

In recent years, it is common to periodically observe and measure the biomarkers of a variety of diseases in order to prevent disease, suppress the progression of disease, or monitor health. For instance, diabetic patients have to measure the blood sugar concentration (blood sugar level) three or four times a day. Hyperlipidemia patients have to regularly measure blood cholesterol levels and neutral fat levels, although less frequently than with the blood sugar concentration. Therefore, there is a demand for the development of a handy medical measurement device which can be used by normal people who are not health-care workers.

Blood components are usually measured for blood sugar concentration or blood cholesterol levels after the blood is drawn through a person's skin. However, because blood drawing is painful and involves troublesome operations, such as the sterilization of the blood drawing area and the instruments, and for other reasons too, there is a need for a non-invasive method for measuring membranes (biomembranes), such as the human skin and the retina of a living body. The development of such a non-invasive measurement method is a common issue in the entire field of medicine.

An effective non-invasive method for obtaining information of the components inside a biomembrane is a measurement of the spectral characteristics using a near-infrared light which adequately penetrates the skin. However, when measuring a biomembrane, the object to be measured inevitably moves due to breathing and the beating of the heart. In addition, blood sugar level sensors or other devices for use in daily life are required to be small, portable, and inexpensive.

As a technology for measuring spectral characteristics, methods using the spectroscopic technology known as a wavelength-dispersive spectroscopy or a Fourier spectroscopy have been proposed (refer to Non-Patent Document 1).

The wavelength-dispersive spectroscopy uses the principle that: when a light passing through, or reflected on the surface of, a sample to be measured (which is referred to as an "object light" hereinafter) is delivered to a diffraction grating, its diffraction angle differs depending on the wavelength of the object light.

The Fourier spectroscopy is a spectroscopic measurement technology using a phase-shift interferometry by means of a Michelson-type two-beam interference optical system. Object light is divided into two beams by a beam splitter such as a half mirror, and each beam is reflected by a mirror and delivered again to the half mirror, where both beams merge with each other and the interference phenomenon is observed. The mirror which reflects one (reference light) of the two divided beams is called a reference mirror. In the Fourier spectrometry, the reference mirror is moved with high precision, i.e. with a resolution smaller than the wavelength of light so as to change the intensity of the interfering light, whereby a so-called interferogram is detected. The interferogram is mathematically Fourier-converted to obtain the spectral characteristics.

The object light rays emitted from the surface of the sample to be measured go in a variety of directions due to scattering, refraction, reflection, and other factors. If the light components of various directions are delivered to a diffraction grating and a reference mirror, the spectral accuracy will be deteriorated. Considering this factor, in any spectroscopies, in order to enhance the spatial coherency of the object lights, a pinhole or a slit with a minute opening is used so that only the light component of a specific direction of the object light is delivered to the diffraction grating and the reference mirror. A pinhole having a diameter of tens of microns is used for the dispersive spectroscopy, while a slit having a width of a few millimeters is used for the Fourier spectrometry, although their sizes depend on the required spectral performances.

When a pinhole or a slit is used, most of the object light does not pass through the pinhole or the slit and will not be used for measurement. That is, light efficiency is low. The scattered light and other light generated inside a biomembrane are weak. Conventional spectroscopic techniques are not suitable for a weak light measurement, and therefore it is difficult to observe light scattered in an arbitrary position inside a biomembrane and evaluate its spectral characteristics.

In view of this, the inventor of the present invention has proposed a method for obtaining the interferogram of an object to be measured by using the phenomenon of interference between the beams from the object (object beams), which are generated at each of the bright point that optically constitute the object to be measured (refer to Patent Document 1).

In this method, the light rays generated at each bright point are introduced to a fixed mirror unit and a movable mirror unit of a phase-changeable filter by way of an objective lens. The movable mirror unit is driven by a piezo element or other element. The object beams reflected by these two mirror units form an interference image on the imaging plane. The intensity of the interference image changes as the movable mirror unit moves, thereby forming a so-called interferogram. By Fourier-transforming the interferogram, the spectral characteristics (spectrum) of the transmitted light or diffused/scattered light can be obtained.

In the method according to Patent Document 1, all the rays which have passed through the objective lens can be used for a measurement. That is, the light efficiency is high and therefore the method is suitable for a weak light measurement. In addition, this method does not require a beam splitter, which is an inevitable component for a two-beam interferometer as typified by a Michelson interferometer. That is, the use of reflective lenses for the objective lens and the imaging lens enables the provision of a spectral device employing a reflection optical system. In this case, since the adverse effects of the light dispersion due to transmissive optical elements is avoided, the spectral characteristics across a wide band can be obtained.

BACKGROUND ART DOCUMENT

Patent Documents

[Patent Document 1] JP-A 2008-309706

Non-Patent Documents

[Non-Patent Document 1] "Fourier Henkan Sekigai Bunkoho (Fourier-transform Infrared Spectrometry)", edited by Hiraishi Jiro, Gakkai Shuppan Center, November 1985

DISCLOSURE OF THE INVENTION

Problem to be Solved by the Invention

However, in the method of Patent Document 1, operation of the movable mirror section requires high accuracy and a high degree of straightness of movement. Therefore, it is necessary to use an expensive driving mechanism such as an accurate piezo stage. In addition, the use of the driving mechanism increases the size of the device. Further, though mechanical scanning of the movable mirror section is favorable in terms of the spatial resolution, but it is not necessarily a good method in terms of the temporal resolution.

The problem to be solved by the present invention is to provide a small and portable spectroscopic measurement device and a spectroscopic measurement method which can shorten the measurement time.

Means for Solving the Problem

To solve the aforementioned problem, the first aspect of the present invention provides a spectroscopic measurement device, including:
  a) a division optical system for joining light rays emitted in a variety of directions from a measurement point of an object to be measured to form a beam, and for dividing the beam into a first beam and a second beam;
  b) an imaging optical system for focusing the first beam and the second beam on a single line that extends in a direction which is different from those of optical axes of the first beam and the second beam so as to form a linear interference image;
  c) an optical path length difference changer for giving a continuous chane of an optical path length difference between the first beam and the second beam;
  d) a detection unit for detecting a light intensity distribution of the linear interference image along the interference image; and
  e) a processing unit for obtaining an interferogram of the measurement point of the object to be measured based on the light intensity distribution of the interference image detected by the detection unit, and for Fourier-converting the interferogram to obtain a spectrum.

The second aspect of the present invention, which has another configuration and yet is based on the same principle as the first aspect of the present invention, provides a spectroscopic measurement device, including:
  a) a division optical system for joining light rays emitted in a variety of directions from a measurement point of an object to be measured to form a beam, and then for dividing the beam and directing the divided beams to a first reflection unit and a second reflection unit;
  b) an imaging optical system for focusing a first reflected beam, which has been reflected by the first reflection unit, and a second reflected beam, which has been reflected by the second reflection unit, on a single line that extends in a direction which is different from those of optical axes of the first reflected beam and the second reflected beam so as to form a linear interference image;
  c) an optical path length difference changer for giving a continuous change of an optical path length difference between the first reflected beam and the second reflected beam;
  d) a detection unit for detecting a light intensity distribution of the linear interference image along the interference image; and
  e) a processing unit for obtaining an interferogram of the measurement point of the object to be measured based on the light intensity distribution of the interference image detected by the detection unit and for Fourier-converting the interferogram to obtain a spectrum.

The third aspect of the present invention provides a spectroscopic measurement device, including:
  a) a division optical system for joining light rays emitted in a variety of directions from a measurement point of an object to be measured to form a beam and dividing the beam into a first beam and a second beam;
  b) an imaging optical system for focusing the first beam and the second beam on a single line that extends in a direction which is different from those of optical axes of the first beam and the second beam so as to form a linear interference image;
  c) an optical path length difference changer for giving a continuous change of an optical path length difference between the first beam and the second beam;
  d) a spectral optical system for wavelength-resolving the linear interference image to form an optical spectrum; and
  e) a detection unit for detecting a light intensity distribution of the optical spectrum.

The fourth aspect of the present invention, which has another configuration and yet is based on the same principle as the first aspect of the present invention, provides a spectroscopic measurement device, including:
  a) a division optical system for joining light rays emitted in a variety of directions from a measurement point of an object to be measured to form a beam, and then for dividing the beam and directing the divided beams to a first reflection unit and a second reflection unit;
  b) an imaging optical system for focusing a first reflected beam, which has been reflected by the first reflection unit, and a second reflected beam, which has been reflected by the second reflection unit, on a single line that extends in a direction which is different from those of an optical axes of the first reflected beam and the second reflected beam so as to form a linear interference image;
  c) an optical path length difference changer for giving a continuous change of an optical path length difference between the first reflected beam and the second reflected beam;
  d) a spectral optical system for wavelength-resolving the linear interference image to form an optical spectrum; and
  e) a detection unit for detecting a light intensity distribution of the optical spectrum.

The fifth aspect of the present invention provides a spectroscopic measurement method including the steps of:
  a) dividing light rays emitted in a variety of directions from each measurement point of an object to be measured into reference multiple rays and oblique multiple rays by means of a division optical system;
  b) giving a continuous change of an optical path length difference between the reference multiple rays and the oblique multiple rays, and focusing the reference multiple rays and the oblique multiple rays on a single line by means of an imaging optical system so as to form a linear interference image; and c) obtaining an interferogram of the measurement point of the object to be measured based on a light intensity distribution of the linear interference image along the interference image, and Fourier-converting the interferogram to obtain a spectrum.

The sixth aspect of the present invention provides a spectroscopic measurement method including the steps of:

a) dividing light rays emitted in a variety of directions from each measurement point of an object to be measured into reference multiple rays and oblique multiple rays by means of a division optical system;

b) giving a continuous change of an optical path length difference between the reference multiple rays and the oblique multiple rays, and focusing the reference multiple rays and the oblique multiple rays on a single line by means of an imaging optical system so as to form a linear interference image; and c) wavelength-resolving the linear interference image by means of an imaging optical system so as to obtain an optical spectrum.

Effects of the Invention

The spectroscopic measurement device and the spectroscopic measurement method according to the present invention use an imaging optical system. The light rays generated at each of the bright points which optically constitute the object to be measured are divided by a division optical system, and the phenomenon of interference between the divided object beams is used to obtain the interferogram of the object to be measured. The term "division optical system" means a system for simply dividing the light rays from the bright points, whereas "spectral optical system" means a system for optically dividing a light according to the wavelength.

In the present invention, all the beams which have passed through the division optical system can be used for an analysis. Therefore, the spectroscopic measurement device and the spectroscopic measurement method according to the present invention have a very high light efficiency and are suitable for a weak light measurement. In this case, the "the beams which have pass through" includes "the beams which have penetrate" and "the beams which have reflected."

In the present invention, the light intensity of an interference image is detected just once so that interferogram which is based on the light intensity change of the interfering image is obtained. This shortens the time required for a spectroscopic measurement. Therefore, the measurement is less likely to be affected by mechanical vibrations and other factors that are present while the measurement is in progress, which can increase the measurement accuracy.

In addition, in contrast to conventional configurations, the present invention does not require a driving mechanism for providing a change of an optical path length difference between the first beam and the second beam (the first reflected beam and the second reflected beam). This allows the downsizing of the device, and a portable spectroscopic measurement device can be provided.

The present invention uses an imaging optical system for focusing the first beam (the first reflected beam) and the second beam (the second reflected beam) on a single line so as to form a linear interference image. Therefore, in the case of obtaining the spectrum of the light emitted from one measurement point of an object to be measured, a detection device as the detection unit in which a plurality of pixels are one-dimensionally (linearly) arranged is required. In the case of obtaining the spectrum of the light emitted from a plurality of measurement points which are linearly positioned on an object to be measured, a detection device as the detection unit in which a plurality of pixels are two-dimensionally arranged is required. In other words, using a one-dimensional detection device as the detection unit enables the acquisition of the spectrum of one measurement point of the object to be measured, while using a two-dimensional detection device enables the simultaneous acquisition of the spectra of a linearly-arranged plurality of measurement points on the object to be measured.

It is known that the spatial resolution of an imaging optical system is generally proportional to $\lambda/NA$, where $\lambda$ denotes the wavelength of light, and NA denotes the numerical aperture of the objective lens. That is, using an objective lens with a high value of NA increases the resolution. The resolution can be enhanced further through combined usage with a super-resolution technology, such as an immersion lens or off-axis illumination.

In the present invention, the division optical system joins light rays emitted in a variety of directions from a measurement point of an object to be measured to form a beam, and then divides the beam into two beams. Hence, by uniting the light rays from the measurement point to form a beam using an objective lens, for example, it is possible to measure the spectral characteristics of only the rays which are emitted from the focal point of the objective lens and which are used to form an image. Therefore, moving the focal point by moving the objective lens or the sample in the direction of focal depth enables the three-dimensional spectral characteristics of the sample to be obtained.

Since the focal depth is proportional to $\lambda/NA^2$ and as it is optically determined, using a high NA optical system utilizing a super-resolution technology can easily enhance the spatial resolution in the depth direction.

BEST MODES FOR CARRYING OUT THE INVENTION

Figure 1:
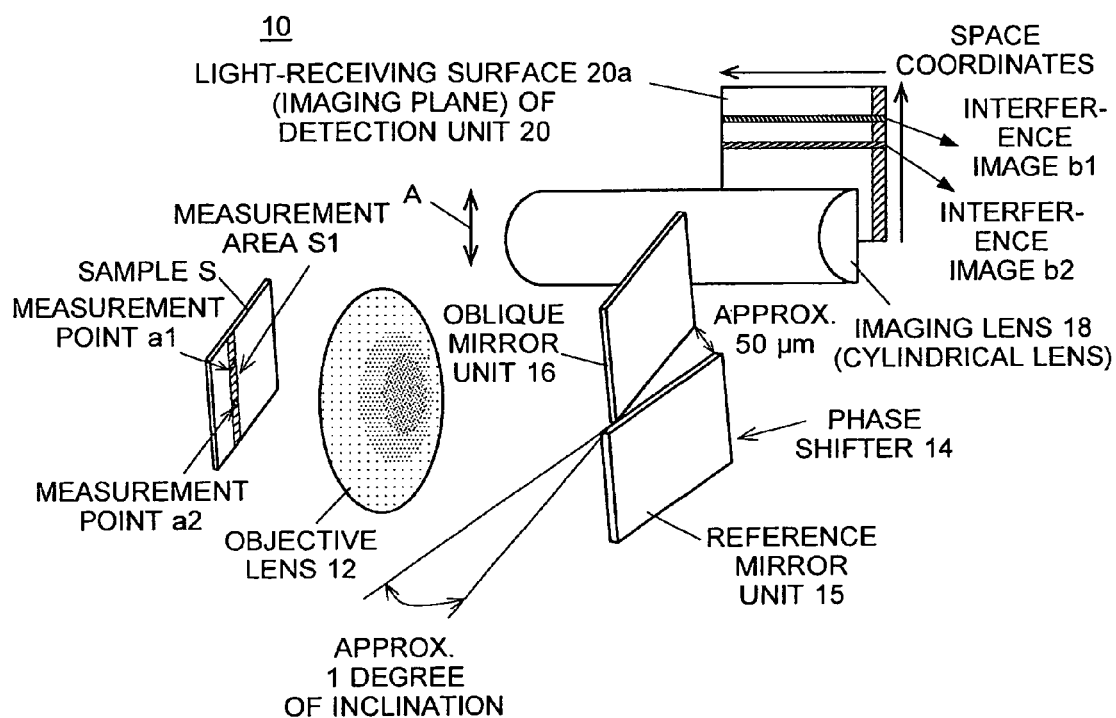
FIG. 1 is an overall configuration diagram of a spectroscopic cross-sectional image measurement device according to the first embodiment of the present invention.

When a light is delivered onto an object, a variety of optical phenomena such as reflection, refraction, scattering, and fluorescence cause object lights to be generated. By using the generated lights to optically model the object, the object can be regarded as a mass of bright points which are ideal light point sources. Rays of light are radially emitted from one bright point as an ideal light source point, although the directionality varies depending on the method of illumination and the optical phenomenon which generates the object lights. The imaging optical system forms an image of an optical conjugate group of a group of bright points optically constituting an object, by reconstituting it on an imaging plane using a lens.

In the cases of fluorescent rays and scattered rays, the initial phases of the rays are not always the same among the bright points. In other words, in an optical model, it is possible to consider that many bright points having different initial phases are distributed on an object. In consideration of the optical paths of the rays in the imaging optical system from the surface of the object to the imaging plane, multiple rays emitted from one of the bright points which optically constitute the object are focused with the same phase on the imaging plane. In this case, in a general imaging optical system, multiple rays generated at one bright point are focused on one point on the imaging plane to form an image. However, if a cylindrical lens is used as the imaging lens, the multiple rays generated at one bright point are focused on a line on the imaging plane to form an image.

In the present invention, by means of the division optical system, the object lights generated at each bright point which optically constitute the object are divided into two beams of multiple rays. Then, the two beams of multiple rays are focused on the same line on the imaging plane to form an image. The interference light intensity distribution (imaging intensity distribution) of the linear interference image formed on the imaging plane by the interference phenomenon between these beams of multiple rays is detected in the direction of the interference image by the detection unit. If the relative optical path difference between the two beams of multiple rays which form the linear interference image continuously changes (increases or decreases) from one end to the other end of the linear interference image for example, the interference light intensity of the lights with a variety of wavelengths which compose each of the beams of multiple rays periodically changes according to the wavelength. Therefore, by detecting the interference light intensity distribution in the direction of the interference image, an interferogram can be obtained. By Fourier-converting this interferogram, the spectral characteristics (spectrum), which shows the relative intensity for each wavelength, can be obtained.

In place of measuring the light intensity distribution of the interference image, the interference image may be waveform-resolved using a spectral optical system, such as a cylindrical lens and a diffraction grading. In this case, an optical spectrum can be optically obtained without having to perform a mathematical Fourier-conversion, which can further reduce the time for the spectral measurement.

Hereinafter, specific embodiments will be described in which the present invention is applied to a spectroscopic cross-sectional image measurement device, which is a spectroscopic measurement device. The below-described embodiments can be applied, for example, in a device for measuring the blood components based on the spectral characteristics of the transmitted lights and scattered lights emitted from a palm of a test subject when a light of a wavelength with a good permeability to the skin is delivered onto the palm, or a device for measuring, when glycoprotein on the surface layer of a cell membrane is labeled with a quantum dot, the distribution of the glycoprotein based on the spectral characteristics of the fluorescence emitted from the quantum dot. The embodiments can also be applied for a fundus imaging device for examining the blood vessels, the retina, optic nerves, and other portions of an eyeground.

First Embodiment

Figure 2A:
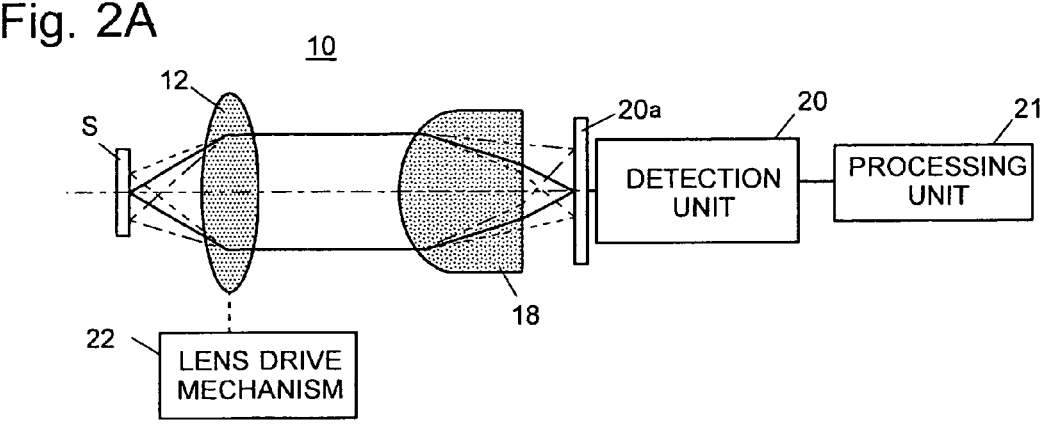
FIG. 2A is a side view schematically showing the spectroscopic cross-sectional image measurement device.
Figure 2B:
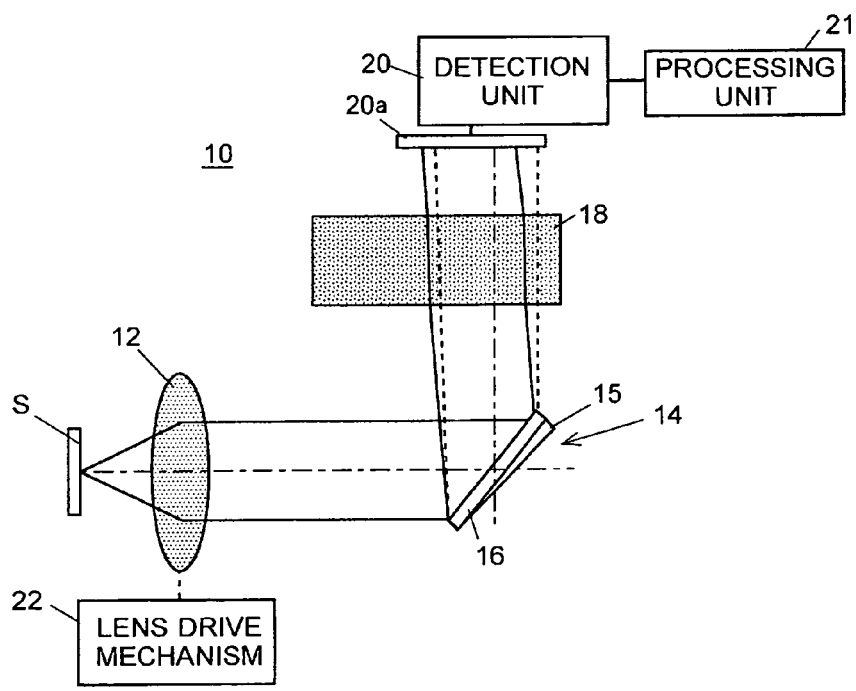
FIG. 2B is a top view showing the spectroscopic cross-sectional image measurement device.

FIGS. 1 through 4 show the first embodiment of the present invention. As shown in FIGS. 1 and 2, the spectroscopic cross-sectional image measurement device 10 according to the first embodiment has: an objective lens 12; a phase shifter 14; an imaging lens (cylindrical lens) 18; a detection unit 20, which has a light-receiving surface 20a at the position serving as the imaging plane; and a processing unit 21 for processing the detection signals from the detection unit 20. In FIG. 2A, the phase shifter 14 is omitted for ease of explanation.

The objective lens 12 can be moved in the direction of its optical axis by means of a lens drive mechanism 22. The lens drive mechanism 22 is used for shifting the focal point of the objective lens, and corresponds to the focal point changer of the present invention. The lens drive mechanism 22 may be configured by a piezo element for example.

When a light from a light source (not shown) is delivered onto a linear measurement area S1 on a sample S (an object to be measured), multiple rays (which are also referred to as the "object lights") such as scattered lights and fluorescent lights are emitted radially in a variety of directions from each bright point in the measurement area S1. The multiple rays enter the objective lens 12, where they are converted into a parallel beam.

The beam after passing through the objective lens 12 does not have to be a perfect parallel beam. As will be described later, the objective lens 12 just has to widen the multiple rays generated at a bright point so that they can be divided into two or more beams. However, a non-parallel beam is likely to cause an error in the amount of phase difference, which depends on the phase shift amount (which will be described later). Therefore, it is preferable to use a parallel beam in order to enhance the accuracy of spectroscopic measurement.

The parallel beam which has been passed through the objective lens 12 reaches a phase shifter 14. The phase shifter 14 includes: a reference mirror unit 15; an oblique mirror unit 16; a holder (not shown) for holding the mirror units 15 and 16; and other units. The surfaces (reflection surfaces) of the reference mirror unit 15 and the oblique mirror unit 16 are optically flat and are rectangular optical mirror surfaces which can reflect the light of the wavelengths to be measured by the device 10. The sizes of the reflection surfaces of the reference mirror unit 15 and the oblique mirror unit 16 are the same.

In the case where the texture of the object is one-sided, the lights (object lights) generated at each of the bright points which optically constitute the object are directed only in a specific direction. Hence, the light amount distribution of the parallel beam which reaches the phase shifter 14 will be uneven. This might prevent the light amount distribution on the light-receiving surface 20a which is the imaging plane from being even. In contrast, in the case where the texture of the object is relatively uneven, the object lights which reach the phase shifter 14 have an even light amount distribution thereon. In the following explanation, suppose that the texture of the sample S is relatively uneven, that the beam which arrives at the phase shifter 14 has an even light amount distribution thereon, and that the same amount of beam is delivered onto the reflection surfaces of the reference mirror unit 15 and the oblique mirror unit 16.

In the present embodiment, the objective lens 12 and the phase shifter 14 correspond to the division optical system of the present invention. The phase shifter 14 corresponds to the optical path length difference changer of the present invention. The reference mirror unit 15 and the oblique mirror unit 16 correspond to the first reflection unit and the second reflection unit, respectively.

In the description below, of the beams which have reached the phase shifter 14, the beam which reaches and is reflected by the reflection surface of the reference mirror unit 15 will also be referred to as reference multiple rays, and the beam which reaches and is reflected by the reflection surface of the oblique mirror unit 16 will also be referred to as oblique multiple rays.

The reference mirror unit 15 is positioned so that its reflection surface is inclined at 45 degrees, for example, with respect to the optical axis of the parallel beam coming from the objective lens 12. The oblique mirror unit 16 is positioned so that its reflection surface is inclined at $(45+\Delta\theta)$ degrees with respect to the optical axis of the parallel beam coming from the objective lens 12. This oblique positioning of the reference mirror unit 15 and the oblique mirror unit 16 with respect to the parallel beam coming from the objective lens 12 can eliminate a beam splitter for dividing the beam. Although the objective lens 12 is used in this embodiment, this function can be realized by using a reflection optical system. Since this configuration can eliminate any influence of the dispersion, the spectral characteristics across a wide band can be measured.

The inclination angle, $\Delta\theta$, of the oblique mirror unit 16 with respect to the reference mirror unit 15 is determined by the optical conditions, such as the magnification of the imaging optical system, the measuring wavelength range, and the wavenumber resolution. For example, consider the case where the measuring wavelength is from the visible range to the near-infrared range (400 through 1000 nm). In order to obtain the wavenumber resolution of $\lambda^2/\Delta\lambda=5$ nm, since the central wavelength is $\lambda=700$ nm, the phase shift amount is $\Delta\lambda=100$ μm. In the case where a CCD camera is used as the detection unit (light-receiving element), the number of pixels in approximately one line is about 500. Therefore, if the phase shift amount per line is 100 μm, the phase difference amount per pixel is 200 nm, which enables a measurement of the wavelength up to 400 nm by a sampling theorem. Since the measuring wavelength is within the visible range (400 through 1000 nm) as described above, if the phase difference amount per pixel is 200 nm, the sampling theorem on the short wavelength side is satisfied.

The maximum distance between the reference mirror unit 15 and the oblique mirror unit 16 may be set at half the value of the 100 μm phase shift amount per line of a CCD camera, i.e. 50 μm (100 μm/2). For example, in the case where the length along the optical path direction (the inclined direction of each mirror unit) of each of the mirror units is approximately 3 mm, the inclination angle is approximately 1 degree.

Particularly in a long-wavelength region for mid-infrared lights, not only the interference intensity change of the interferogram, but also the envelope of the interference intensity change must be obtained in a long-stroke phase shift region. This is also understood from the principle of Fourier spectroscopy that a large phase shift amount is required to increase the wavenumber resolution. Detecting the envelope of the interferogram for a long stroke requires that the oblique mirror unit 16 has a large inclination angle. In this case, an inclination change mechanism for two modes, for example, may be provided to detect the interference intensity change of the interferogram and to detect the envelope. In the case where the envelope is measured in the mid-infrared region, since the required phase shift amount is approximately 50 mm, for example, the length along the optical path direction may be lengthened to 100 mm and the inclination angle may be set at 2.9 degrees, for example.

Both the reference multiple rays and the oblique multiple rays which have arrived at the phase shifter 14 and have been reflected at the reflection surfaces of the reference mirror unit 15 and the oblique mirror unit 16 enter the imaging lens 18. The imaging lens 18 is provided so that its convex surface side faces the phase shifter 14 and its plain side faces the light-receiving surface 20a of the detection unit 20. The light-receiving surface 20a of the detection unit 20 is placed on the imaging plane of the imaging lens. Hence, the reference multiple rays and the oblique multiple rays which have been emitted from a bright point in the measurement area S1, reflected at the reflection surfaces of the reference mirror unit 15 and the oblique mirror unit 16, and then entered the imaging lens 18 are focused only in one direction by the imaging lens, and collected on the same line on the light-receiving surface 20a of the detection unit 20, thereby forming an image. In the present embodiment, suppose that the imaging lens 18 provided so that the direction (which is indicated by an arrow A in FIG. 1) in which the convex surface is curved is parallel to the direction of the measurement area S1. Because of this configuration, the reference multiple rays and the oblique multiple rays which have entered the imaging lens 18 are focused on the straight line which is on the light-receiving surface 20a and is perpendicular to the measurement area S1.

The detection unit 20 is composed of a two-dimensional CCD camera, for example. The reflection surface of the reference mirror unit 15 and that of the oblique mirror unit 16 are provided so as to be relatively parallel to each other to the degree with which the light-focusing positions of these two multiple rays are not displaced in relation to each other on the imaging plane of the detection unit 20.

The optical effect of the spectroscopic cross-sectional image measurement device 10 having the above-described configuration is now described.

The explanation is based on the following optical model. Multiple rays which do not always have the same initial phase, such as fluorescent lights and scattered lights, pass through the objective lens 12 where they are collimated into parallel rays. Then the beam is divided into reference multiple rays and oblique multiple rays by the phase shifter 14. Of the two multiple rays, the reference multiple rays are focused, by the imaging lens, as waves having the same phase on a straight line on the light-receiving surface 20a of the detection unit 20. In this case, the oblique multiple rays are focused as waves whose phase gradually differs from that of the reference multiple rays on a straight line on the light-receiving surface 20a.

As previously described, the multiple rays emitted from a bright point in the measurement area S1 of the sample S pass through the objective lens 12 and reach the surfaces of the reference mirror unit 15 and the oblique mirror unit 16 of the phase shifter 14. In this case, the multiple rays are vertically divided in two beams, and the beams reach the surface of the reference mirror unit 15 and that of the oblique mirror unit 16. The surface areas of the minor units 15 and 16 are set so that the amount of light of the multiple rays which have reached the surface of the reference mirror unit 15 (i.e. the reference multiple rays) is substantially the same as that of the multiple rays which have reached the surface of the oblique minor unit 16 (i.e. the oblique multiple rays). However, a dark filter may be provided on one or both of the optical paths of the reference multiple rays and the oblique multiple rays so as to adjust the relative light amount difference, thereby equalizing their amounts of light.

Figure 3:
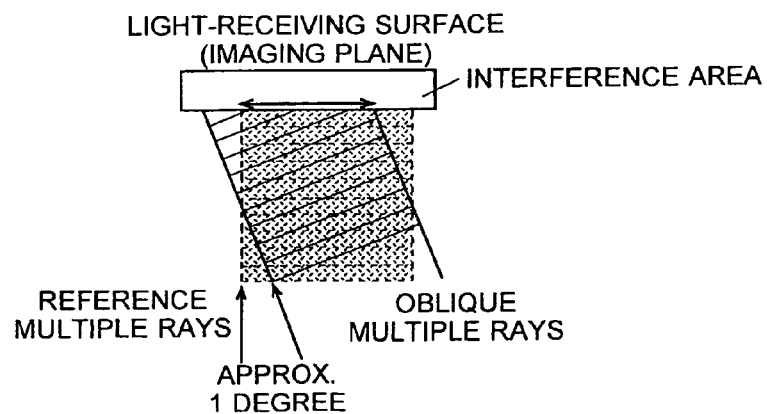
FIG. 3 shows an image of the interference between reference multiple rays and oblique multiple rays in the first embodiment.

The multiple rays reflected on the surface of the reference mirror unit 15 and the oblique mirror unit 16 enter the imaging lens 18 as reference multiple rays and oblique multiple rays. The reference multiple rays and the oblique multiple rays are focused on the same straight line on the light-receiving surface 20a of the detection unit 29, thereby forming an interference image. Since the reference multiple rays pass through the imaging lens 18 and are focused as waves having the same phase on the light-receiving surface 20a which is an imaging plane, the wavefronts of the reference multiple rays are parallel to the light-receiving surface 20a of the detection unit 20, as shown in FIG. 3. Meanwhile, since the oblique multiple rays enter the imaging lens 18 with the optical axis inclined by $2 \times \Delta\theta°$ with respect to the optical axis of the reference multiple rays, the wavefronts of the oblique multiple rays are a little inclined with respect to the light-receiving surface 20a.

Figure 4A:
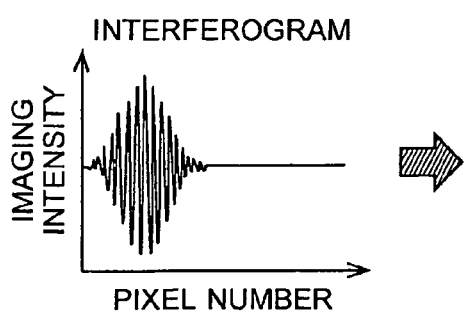
FIG. 4A shows an interferogram.
Figure 4B:
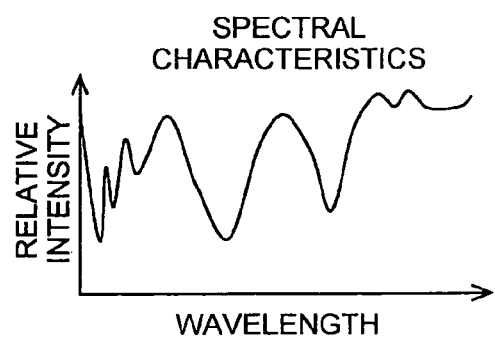
FIG. 4B is a waveform diagram obtained by Fourier-converting the interferogram.

As just described, the wavefronts of the oblique multiple rays are inclined with respect to those of the reference multiple rays. Therefore, in the interference area between the lights of the reference multiple rays and those of the oblique multiple rays, the optical path length difference between the two multiple rays gradually changes (gradually becomes larger from right to left in the example of FIG. 3). Since the multiple rays emitted from the measurement area S1 include lights having a variety of wavelengths (and the initial phases of the lights of each wavelength are not always the same), the optical path length difference between the reference multiple rays and the oblique multiple rays gradually changes in the interference area. Therefore, the waveform of the imaging intensity distribution (interference light intensity distribution) which is called an interferogram as shown in FIG. 4A can be obtained.

For example, as shown in FIG. 1, the multiple rays emitted from a bright point (measurement point) a1 in the measurement area S1 are focused on a straight line on the light-receiving surface 20a (imaging plane) to form a linear interference image b1, while the multiple rays emitted from a bright point (measurement point) a2 are focused on a straight line on the light-receiving surface 20a to form a linear interference image b2. Each of the interferograms of the interference images b1 and b2 is obtained from the intensity of the received light of a plurality of pixels aligned along each interference image. In FIG. 4A, the horizontal axis represents the pixel number of the pixels aligned along the linear interference image of the detection unit 20 and the vertical axis represents the imaging intensity (the intensity of received light). Converting the pixel numbers by the phase shift amount for each pixel can obtain the interferogram in which the horizontal axis represents the phase shift amount.

The processing unit 21 Fourier-converts the interferogram and obtains the spectral characteristics (refer to FIG. 4B), which shows the relative intensities among the wavelengths of the lights emitted from a bright point in the measurement area S1. If the spectral characteristics can be obtained using all the pixels of the detection unit 20, a one-dimensional spectral measurement of the measurement area S1 can be realized. If the measurement area S1 onto which an irradiation light is delivered is scanned, a two-dimensional spectral measurement of the measurement area S1 can be realized. If the measurement area S1 is scanned and the focal plane (the plane including the focal point) is scanned by moving the objective lens 12, a three-dimensional spectral measurement can be realized. This is due to the characteristics of interferograms, in that the depth of the measuring plane can be limited in the focal plane, because an interferogram, which shows the interference intensity change, is created only with object lights from the focal plane that contribute to the formation of an image.

Second Embodiment

Figure 5:
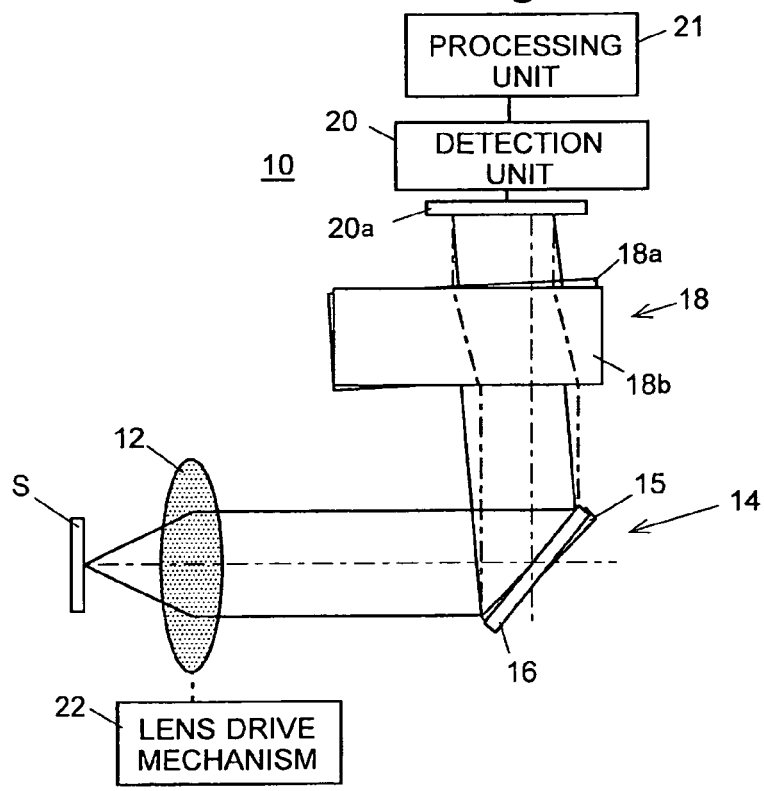
FIG. 5 is a top view schematically showing a spectroscopic cross-sectional image measurement device according to the second embodiment of the present invention.
Figure 6:
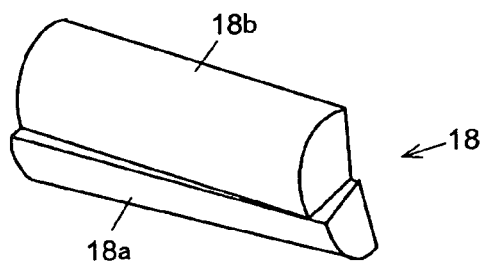
FIG. 6 is a perspective view of an imaging lens according to the second embodiment.
Figure 7:
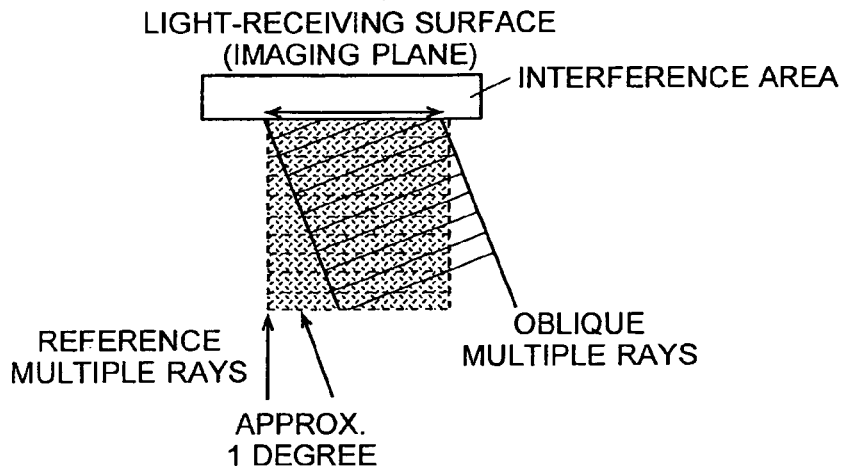
FIG. 7 shows an image of the interference between reference multiple rays and oblique multiple rays in the second embodiment.

FIGS. 5 through 7 show the second embodiment of the present invention. As shown in FIGS. 5 and 6, in the spectroscopic cross-sectional image measurement device 10 according to this embodiment, the imaging lens 18 is divided into a reference lens unit 18a and an oblique lens unit 18b. The reference multiple rays which have been reflected by the reference mirror unit 15 enter the reference lens unit 18a, while the oblique multiple rays which have been reflected by the oblique mirror unit 16 enter the oblique lens unit 18b. The reference lens unit 18a and the oblique lens unit 18b are the same shape as the evenly-divided imaging lens 18 of the first embodiment, and are provided so that the inclination of the optical axis of one of the reference multiple rays and the oblique multiple rays with respect to the optical axis of the other multiple rays is maintained, while the optical axis of the other multiple rays is shifted along the linear interference image formed on the light-receiving surface 20a (imaging plane) of the detection unit 20. In other words, the reference lens unit 18a and the oblique lens unit 18b function as the imaging optical system and the optical axis changer. This configuration can increase the area (i.e. interference area) in which the beam of the reference multiple rays overlaps that of the oblique multiple rays on the light on the light-receiving surface 20a as shown in FIG. 7.

Third Embodiment

Figure 8:
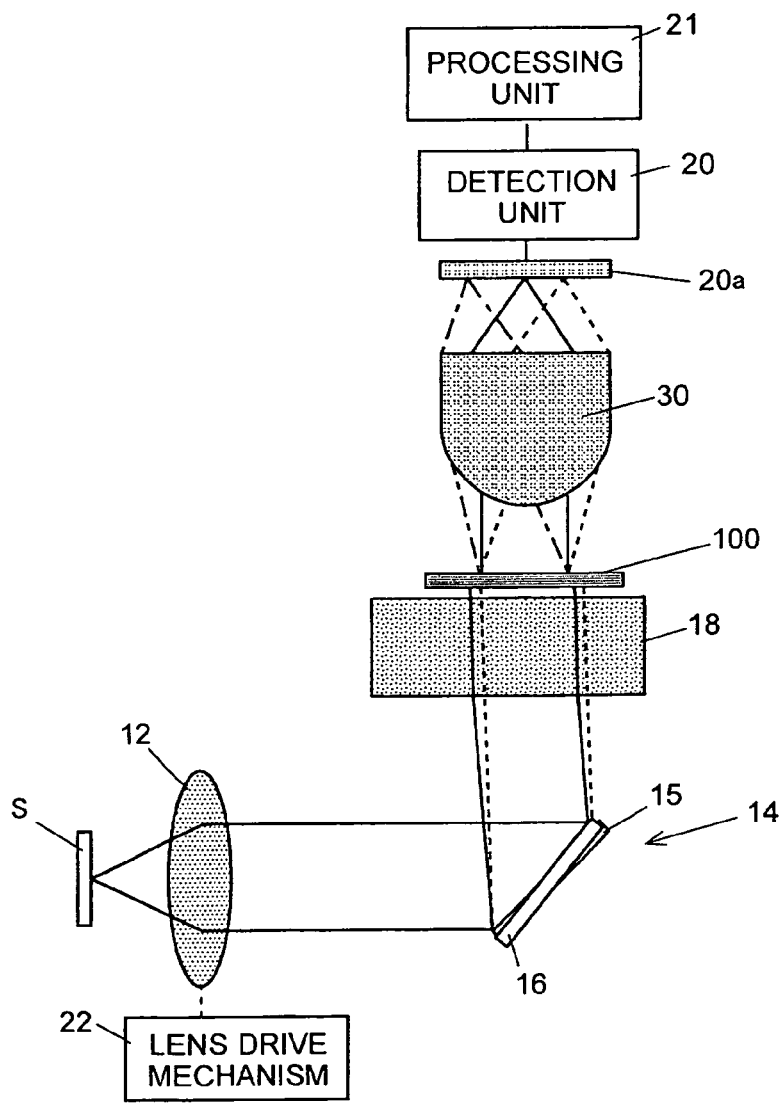
FIG. 8 is a top view schematically showing a spectroscopic cross-sectional image measurement device according to the third embodiment of the present invention.

FIG. 8 shows the third embodiment of the present invention. In the third embodiment, a monochromatic light converter 100, such as a fluorescent plate, for converting a light intensity into a monochromatic light is provided at the position of the imaging plane in the first embodiment, and a cylindrical lens 30 is placed at the position of the monochromatic light converter 100 which is considered as the object plane. The detection unit 20 is placed so that its light-receiving surface 20a is placed on the optical Fourier-conversion plane of the cylindrical lens 30. The cylindrical lens 30 is provided so that the direction of its non-curved portion (its cylindrical axis) is perpendicular to the direction in which the linear interference image extends.

In the third embodiment, the interference image of the reference multiple rays and the oblique multiple rays which have been passed through the imaging lens 18 is converted into a spatial brightness intensity distribution by the monochromatic light converter 100. The intensity distribution is optically Fourier-converted by the cylindrical lens 30, and an optical spectrum is formed on the imaging plane in real time. Since the light-receiving surface 20a of the detection unit 20 is placed on the Fourier-conversion plane of the cylindrical lens 30, optically obtaining the light intensity distribution of the optical spectrum enables an acquisition of the same spectral characteristics as in the case where the interferogram obtained in the first embodiment is mathematically Fourier-converted. That is, in the present embodiment, the spectral characteristics can be directly obtained without having to perform a Fourier-conversion operation, which enables the spectral characteristics to be obtained in a shorter time. In the third embodiment, the monochromatic light converter 100 and the cylindrical lens 30 compose the spectral optical system.

The present invention is not limited to the aforementioned embodiments, and a variety of changes are possible.

A portion of the multiple rays which have been emitted form a measurement point of the object to be measured and then converted into parallel rays by the objective lens may be directed straight to the imaging optical system (cylindrical lens), while the remaining multiple rays may be directed to the imaging optical system through a wedge-shaped glass plate. Also with this configuration, the lights emitted from the measurement point in a variety of directions can be divided in two beams, and a continuous change of an optical path length difference can be given between the two divided beams. That is, in this configuration, the objective lens and the wedge-shaped glass plate compose the division optical system, and the wedge-shaped glass plate composes the optical path length difference changer.

A diffraction grating may be used in place of the monochromatic light converter 100. For example, in the case where a transmission diffraction grating is provided in place of the monochromatic light converter 100, the interference image of the reference multiple rays and the oblique multiple rays is wavelength-resolved by dispersion. Therefore, the intensity distribution for wavelengths can be obtained on the light-receiving surface 20a of the detection unit 20. In this configuration, the diffraction grating composes the spectral optical system.

Using a spectral optical system such as a cylindrical lens and a diffraction grating enables a very quick measurement of the spectral characteristics in which the measurement depth is limited on the focal plane of the objective lens which composes the division optical system.

In the aforementioned embodiments, the phase shifter is composed of the reference mirror unit and the oblique mirror unit, both of which have a rectangular optical mirror surface. However, the phase shifter may be composed of a first mirror (first reflection unit) having a disk-shaped optical mirror surface and a donut-shaped second mirror (second reflection unit) which is placed at the outer periphery of the first mirror. The inner circumference and the outer circumference of the second mirror are a concentric circle of the first mirror, and the second mirror is relatively inclined with respect to the first mirror. Composing the phase shifter from mirrors having such a shape of the optical mirror surface enables a uniform light amount distribution on the imaging plane even in the case where the texture of the object to be measured is one-sided and therefore the light amount distribution of the parallel beam which arrives at the phase shifter is uneven.

Figure 9:
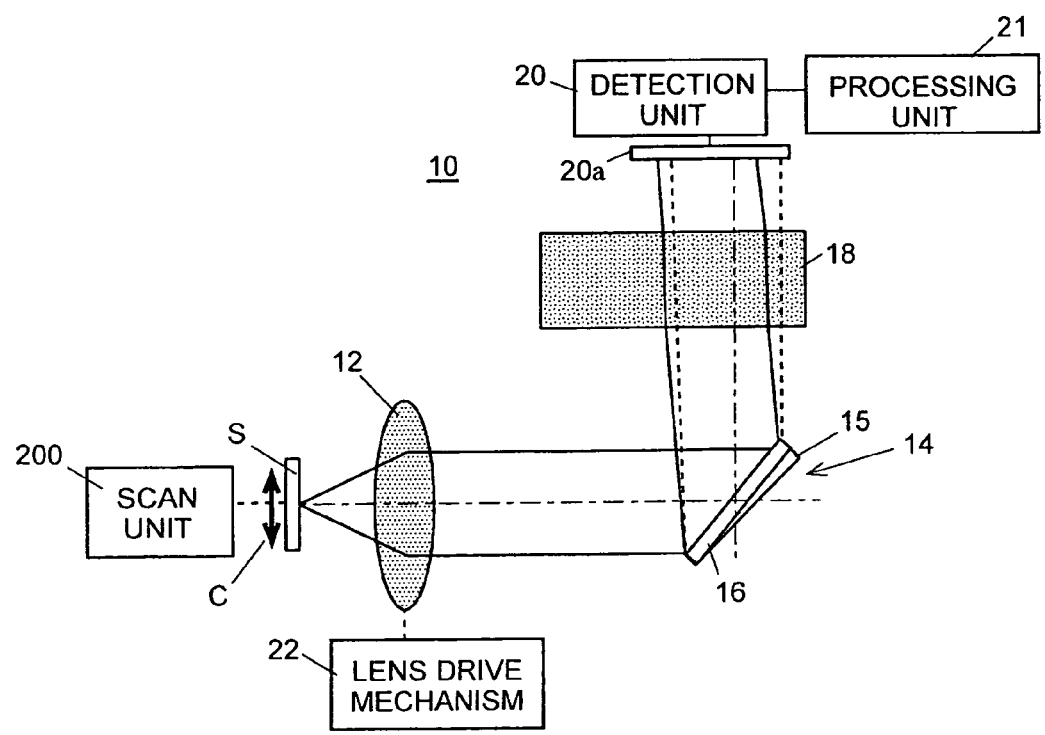
FIG. 9 is a top view schematically showing a spectroscopic cross-sectional image measurement device according to a modification example of the present invention.

As shown in FIG. 9, a scan unit 200 for moving the sample S (object to be measured) in the direction of the arrow C may be provided so as to scan the measurement area S1.

EXPLANATION OF NUMERALS

10 . . . Spectroscopic Cross-Sectional Image Measurement Device
12 . . . Objective Lens
14 . . . Phase Shifter
15 . . . Reference Mirror Unit
16 . . . Oblique Mirror Unit
18 . . . Imaging Lens
  18a . . . Reference Lens Unit
  18b . . . Oblique Lens Unit
20 . . . Detection Unit
  20a . . . Light-Receiving Surface
21 . . . Processing Unit
22 . . . Lens Drive Mechanism
30 . . . Cylindrical Lens
100 . . . Monochromatic Light Converter
200 . . . Scan Unit

The invention claimed is:

1. A spectroscopic measurement for measuring an object, comprising:
  a) a division optical system configured to join light rays emitted in a variety of directions from a measurement point of the object to form a beam, and configured to divide the beam into a first beam and a second beam;
  b) an optical path length difference changer configured to provide a continuous change of an optical path length difference between the first beam and the second beam;
  c) an imaging optical system configured to focus the first beam and the second beam on a single line that extends in a direction which is different from an optical axis of the first beam and an optical axis of the second beam so as to form a linear interference image, wherein the first beam and the second beam enter into the imaging optical system separately;
  d) a detection unit configured to detect a light intensity distribution of the linear interference image along the interference image; and
  e) a processing unit configured to obtain an interferogram of the measurement point of the object based on the light intensity distribution of the interference image detected by the detection unit, and configured to Fourier-convert the interferogram to obtain a spectrum.

2. The spectroscopic measurement device according to claim 1, wherein the division optical system forms a parallel beam and divides the parallel beam into a first parallel beam and a second parallel beam.

3. A spectroscopic measurement device for measuring an object, comprising:
  a) a division optical system configured to join light rays emitted in a variety of directions from a measurement point of the object to form a beam and configured to divide the beam into a first beam and a second beam;
  b) an optical path length difference changer configured to provide a continuous change of an optical path length difference between the first beam and the second beam:
  c) an imaging optical system configured to focus the first beam and the second beam on a single line that extends in a direction which is different from an optical axis of the first beam and an optical axis of the second beam so as to form a linear interference image, wherein the first beam and the second beam enter into the imaging optical system separately;
  d) a spectral optical system configured to wavelength-resolve the linear interference image to form an optical spectrum; and
  e) a detection unit configured to detect a light intensity distribution of the optical spectrum.

4. The spectroscopic measurement device according to claim 3, wherein the division optical system forms a parallel beam and divides the parallel beam into a first parallel beam and a second parallel beam.

5. A spectroscopic measurement for measuring an object, comprising:
  a) a division optical system configured to join light rays emitted in a variety of directions from a measurement point of the object to form a beam, and then configured to divide the beam and configured to direct the divided beams to a first reflection unit and a second reflection unit;
  b) an optical path length difference changer configured to provide a continuous change of an optical path length difference between a first reflected beam and a second reflected beam;

c) an imaging optical system configured to focus the first reflected beam, which has been reflected by the first reflection unit, and the second reflected beam, which has been reflected by the second reflection unit on a single line that extends in a direction which is different from an optical axis of the first reflected beam and an optical axis of the second reflected beam so as to form a linear interference image, wherein the first reflected beam and the second reflected beam enter into the imaging optical system separately;

d) a detection unit configured to detect a light intensity distribution of the linear interference image along the interference image; and e) a processing unit configured to obtain an interferogram of the measurement point of the object based on the light intensity distribution of the interference image detected by the detection unit, and configured to Fourier-convert the interferogram to obtain a spectrum.

6. A spectroscopic measurement device according to claim 5, wherein:

the division optical system has an objective lens for collimating the lights emitted in a variety of directions from the measurement point into a parallel beam and directing the parallel beam to the first reflection unit and the second reflection unit; and the processing unit obtains a spectrum of the lights which have been emitted in a variety of directions from the measurement point in a linear measurement area which is located at a focal point of the objective lens on the object to be measured.

7. The spectroscopic measurement device according to claim 6, comprising a scanner for scanning the linear measurement area.

8. The spectroscopic measurement device according to claim 7, further comprising an optical axis changer for relatively changing an inclination of the optical axis of the second reflected beam which has been passed through the imaging optical system with respect to the optical axis of the first reflected beam which has been passed through the imaging optical system.

9. The spectroscopic measurement device according to claim 6, further comprising an optical axis changer for relatively changing an inclination of the optical axis of the second reflected beam which has been passed through the imaging optical system with respect to the optical axis of the first reflected beam which has been passed through the imaging optical system.

10. The spectroscopic measurement device according to claim 5, comprising an optical axis changer for relatively changing an inclination of the optical axis of the second reflected beam which has been passed through the imaging optical system with respect to the optical axis of the first reflected beam which has been passed through the imaging optical system.

11. The spectroscopic measurement device according to claim 5, wherein:

the division optical system has an objective lens for collimating the lights emitted in a variety of directions from the measurement point into parallel beams and directing the parallel beams to the first reflection unit and the second reflection unit; and the spectroscopic measurement device further comprises a lens drive mechanism that relatively changes a focal point of the objective lens with respect to the object to be measured.

12. The spectroscopic measurement device according to claim 5, wherein the division optical system forms a parallel beam and divides the parallel beam into a first parallel beam and a second parallel beam.

13. A spectroscopic measurement device for measuring an object, comprising:

a) a division optical system configured to join light rays emitted in a variety of directions from a measurement point of the object to form a beam, and then configured to divide the beam and directing the divided beams to a first reflection unit and a second reflection unit;

b) an optical path length difference changer configured to provide a continuous change of an optical path length difference between a first reflected beam and a second reflected beam;

c) an imaging optical system configured to focus the first reflected beam, which has been reflected by the first reflection unit, and the second reflected beam, which has been reflected by the second reflection unit on a single line that extends in a direction which is different from an optical axis of the first reflected beam and an optical axis of the second reflected beam so as to form a linear interference image, wherein the first reflected beam and the second reflected beam enter into the imaging optical system separately;

d) a spectral optical system configured to wavelength-resolve the linear interference image to form an optical spectrum; and e) a detection unit configured to detect a light intensity distribution of the optical spectrum.

14. The spectroscopic measurement device according to claim 13, further comprising an optical axis changer for relatively changing an inclination of the optical axis of the second reflected beam which has been passed through the imaging optical system with respect to the optical axis of the first reflected beam which has been passed through the imaging optical system.

15. The spectroscopic measurement device according to claim 13, wherein:

the division optical system has an objective lens for collimating the lights emitted in a variety of directions from the measurement point into parallel beams and directing the parallel beams to the first reflection unit and the second reflection unit; and the spectroscopic measurement device further comprises a lens drive mechanism that relatively changes a focal point of the objective lens with respect to the object to be measured.

16. The spectroscopic measurement device according to claim 13, wherein the division optical system forms a parallel beam and divides the parallel beam into a first parallel beam and a second parallel beam.

17. A spectroscopic measurement method for measuring an object, comprising the steps of:

a) dividing light rays emitted in a variety of directions from each measurement point of an object into reference multiple rays and oblique multiple rays by a division optical system;

b) providing a continuous change of an optical path length difference between the reference multiple rays and the oblique multiple rays, and focusing the reference multiple rays and the oblique multiple rays on a single line by an imaging optical system so as to form a linear interference image, wherein the reference multiple rays and the oblique multiple rays enter into the imaging optical system separately; and c) obtaining an interferogram of the measurement point of the object based on a light intensity distribution of the linear interference image along the interference image, and Fourier-converting the interferogram to obtain a spectrum.

18. The spectroscopic measurement device according to claim 17, wherein the division optical system forms a parallel beam and divides the parallel beam into a first parallel beam and a second parallel beam.

19. A spectroscopic measurement method comprising the steps of:
   a) dividing light rays emitted in a variety of directions from each measurement point of an object to be measured into reference multiple rays and oblique multiple rays by a division optical system;
   b) providing a continuous change of an optical path length difference between the reference multiple rays and the oblique multiple rays, and focusing the reference multiple rays and the oblique multiple rays on a single line by an imaging optical system so as to form a linear interference image, wherein the reference multiple rays and the oblique multiple rays enter into the imaging optical system separately; and
   c) wavelength-resolving the linear interference image by an imaging optical system so as to obtain an optical spectrum.

20. The spectroscopic measurement device according to claim 19, wherein the division optical system forms a parallel beam and divides the parallel beam into a first parallel beam and a second parallel beam.

\* \* \* \* \*